United States Patent
Fee et al.

(10) Patent No.: US 12,144,657 B2
(45) Date of Patent: Nov. 19, 2024

(54) METHOD AND APPARATUS PROVIDING AN ONGOING AND REAL TIME INDICATOR FOR SURVIVAL AND MAJOR MEDICAL EVENTS

(71) Applicant: AiCare Corporation, San Jose, TX (US)

(72) Inventors: John Fee, Garland, TX (US);
Chih-Hao Liu, Milpitas, CA (US);
Phillip C. Yang, Stanford, CA (US);
Alokkumar Jha, San Jose, CA (US)

(73) Assignee: AiCare Corporation, San Jose, CA (US)

( * ) Notice: Subject to any disclaimer, the term of this patent is extended or adjusted under 35 U.S.C. 154(b) by 427 days.

(21) Appl. No.: 16/900,961

(22) Filed: Jun. 14, 2020

(65) Prior Publication Data

US 2020/0390399 A1 Dec. 17, 2020

Related U.S. Application Data

(60) Provisional application No. 62/861,788, filed on Jun. 14, 2019.

(51) Int. Cl.
*A61B 5/00* (2006.01)
*A61B 5/0205* (2006.01)
(Continued)

(52) U.S. Cl.
CPC .......... *A61B 5/7275* (2013.01); *A61B 5/0022* (2013.01); *A61B 5/02055* (2013.01);
(Continued)

(58) Field of Classification Search
None
See application file for complete search history.

(56) References Cited

U.S. PATENT DOCUMENTS

| | | | |
|---|---|---|---|
| 5,755,671 A * | 5/1998 | Albrecht | A61B 5/0245 600/516 |
| 2005/0010254 A1* | 1/2005 | Zhang | A61B 5/318 607/9 |

(Continued)

OTHER PUBLICATIONS

International Search Report [ISA/US] PCT/US2020/037661 dated Oct. 5, 2020.
(Continued)

*Primary Examiner* — Rene T Towa
*Assistant Examiner* — Aurelie H Tu
(74) *Attorney, Agent, or Firm* — Edwin S. Flores; Daniel J. Chalker; Chalker Flores, LLP

(57) ABSTRACT

The present invention includes a method and apparatus providing an ongoing and real time indicator for prediction of health conditions during the usual lifetime of a person by providing an ongoing and real time indicator for predicting remaining lifetimes for one or more patients comprising: providing a monitoring system connected to the cloud, a Wi-Fi or Bluetooth network which is connected to a wearable device; and providing a wearable device which contains
(Continued)

- Procedures :
  1. Compute daily daytime total energy and nighttime total energy
  2. 1st screening :
     - Calculate 3-day simple moving average for daytime total energy and nighttime total energy
     - Check intersection(s) of these two lines to figure out deceased residents
  3. Obtain daily energy difference (= daytime total energy - nighttime total energy)
  4. Calculate 7-day simple moving average from daily energy difference
  5. Predictive analysis using linear regression model
     - Output: Predicted line and parameters (intercept, slope, and R-squared value)
  6. 2nd screening : Use the positive trend/slope to figure out healthy residents
  7. 3rd screening : Use R-squared value to confirm the deceased and healthy residents one or more accelerometers, temperature monitoring devices, EKG monitoring devices and other useful devices; wherein the wearable device is powered internally by a battery or other such appropriate energy sources.

12 Claims, 15 Drawing Sheets

(51) Int. Cl.
    *G16H 40/67*     (2018.01)
    *G16H 50/30*     (2018.01)
    *A61B 5/11*     (2006.01)
    *A61B 5/332*     (2021.01)

(52) U.S. Cl.
    CPC .......... *A61B 5/4836* (2013.01); *A61B 5/4839* (2013.01); *A61B 5/486* (2013.01); *A61B 5/7267* (2013.01); *A61B 5/746* (2013.01); *A61B 5/7475* (2013.01); *G16H 40/67* (2018.01); *G16H 50/30* (2018.01); *A61B 5/1118* (2013.01); *A61B 5/332* (2021.01); *A61B 2503/08* (2013.01); *A61B 2560/0214* (2013.01); *A61B 2562/0219* (2013.01)

(56) References Cited

U.S. PATENT DOCUMENTS

| | | |
|---|---|---|
| 2010/0249645 A1 | 9/2010 | Semler et al. |
| 2012/0253207 A1* | 10/2012 | Sarkar .................. A61B 5/0006 600/483 |
| 2013/0190903 A1* | 7/2013 | Balakrishnan ......... A63B 71/06 700/91 |
| 2014/0046144 A1* | 2/2014 | Jayaraman ........... G06K 9/0053 600/509 |
| 2015/0282766 A1* | 10/2015 | Cole .................... A61B 5/1123 702/139 |
| 2015/0282767 A1 | 10/2015 | Stivoric et al. |
| 2016/0066838 A1 | 3/2016 | DeCharms |
| 2017/0312515 A1* | 11/2017 | Ferree ................ A61N 1/36021 |

OTHER PUBLICATIONS

Kozina, et al. "Efficient Activity Recognition and Fall Detection Using Accelerometers" Communications in Computer and Information Science • Sep. 2013, DOI: 10.1007/978-3-642-41043-7_2.

* cited by examiner

| | Energy level<br>TP = 3, FP = 0, FN = 0, TN = 8 | (Daily)<br>movement percentage<br>TP = 3, FP = 4, FN = 0, TN = 4 | (Day/Night)<br>movement percentage<br>TP = 2, FP = 0, FN = 1, TN = 8 |
|---|---|---|---|
| Key parameters | 1. Daily daytime/nighttime energy from labeled data<br>2. Compute daily energy difference<br>3. Linear regression model | 1. Daily resting percentage from more1G/2G/3G (without labeled data)<br>2. Daily active percentage ≈ 100 - daily resting percentage | Daytime/nighttime active/resting percentage using more1G/2G/3G counts and labeled data |
| Accuracy = (TP+TN) / (TP+TN+FP+FN) | 100 % | 64 % | 91 % |
| Precision = TP / (TP+FP) | 100 % | 43 % | 100 % |
| Sensitivity (Recall) = TP / (TP+FN) | 100 % | 100 % | 67 % |
| Specificity = TN / (FP+TN) | 100 % | 50 % | 100 % |
| F-measure = 2 * (Precision * Recall)/ (Precision + Recall) | 1 | 0.6 | 0.8 |

Best results

TP: Deceased resident was analyzed to be a deceased resident ; FP: Healthy resident was analyzed to be a deceased resident
FN: Deceased resident was analyzed to be a healthy resident ; TN: Healthy resident was analyzed to be a healthy resident

FIG. 1

- Procedures :
  1. Compute daily daytime total energy and nighttime total energy
  2. 1st screening :
     - Calculate 3-day simple moving average for daytime total energy and nighttime total energy
     - Check intersection(s) of these two lines to figure out deceased residents
  3. Obtain daily energy difference (= daytime total energy - nighttime total energy)
  4. Calculate 7-day simple moving average from daily energy difference
  5. Predictive analysis using linear regression model
     - Output: Predicted line and parameters (intercept, slope, and R-squared value)
  6. 2nd screening : Use the positive trend/slope to figure out healthy residents
  7. 3rd screening : Use R-squared value to confirm the deceased and healthy residents

FIG. 2

- Procedures
  <u>In the Daytime period</u>
  1. In every 5* mins,
     a. TOTAL count = TOTAL count + 1
     b. Check the <u>summation</u> of the counts of more1G, more2G, and more3G
        i. If this summation is equal to 0 => ZERO count = ZERO count + 1
  2. Compute the total numbers of ZERO and TOTAL count within <u>Daytime</u> period
  3. <u>Daytime resting percentage</u> = ZERO count / TOTAL count * 100
     <u>Daytime active percentage</u> = 100% - <u>Daytime resting percentage</u>

FIG. 3A

- Procedures
  <u>In the Nighttime period</u>
  4. In every 5* mins,
     a. TOTAL count = TOTAL count + 1
     b. Check the <u>summation</u> of the counts of more1G, more2G, and more3G
        i. If this summation is equal to 0 => ZERO count = ZERO count + 1
  5. Compute the total numbers of ZERO and TOTAL count within <u>Nighttime</u> period
  6. <u>Nighttime resting percentage</u> = ZERO count / TOTAL count * 100
     <u>Nighttime active percentage</u> = 100% - <u>Nighttime resting percentage</u>

7. Calculate <u>3-day simple moving average(SMA)</u> for 4 parameters
  8. Check intersection(s) of <u>daytime active percentage (with 3-day SMA)</u> and nighttime active percentage <u>(with 3-day SMA)</u> to figure out <u>deceased residents</u>

FIG. 3B

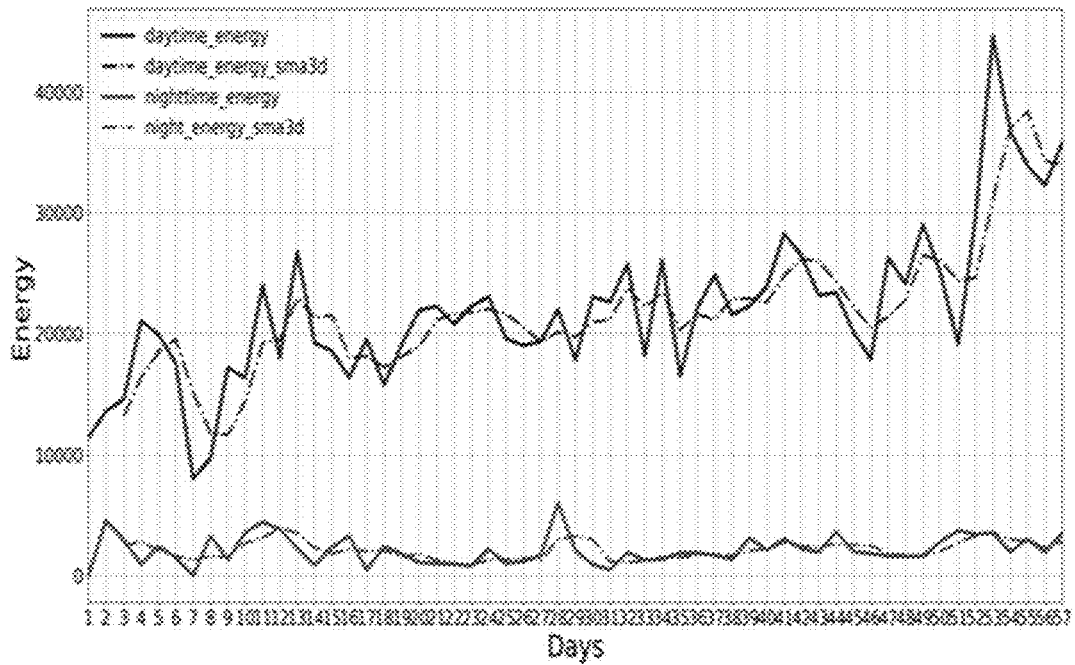
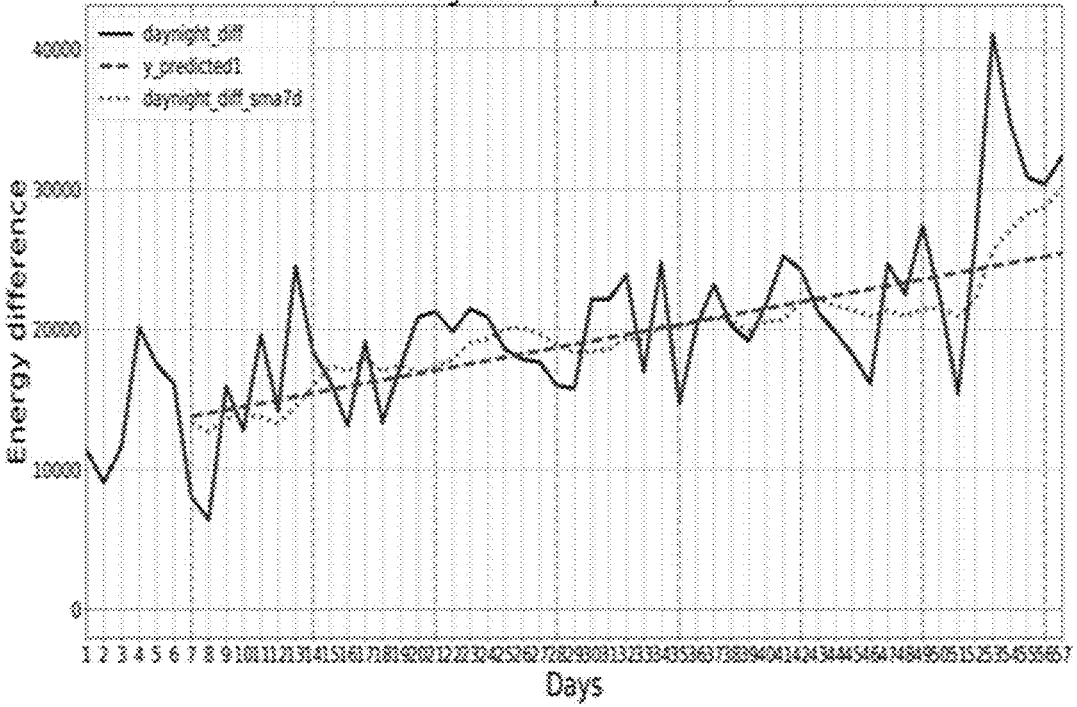
FIG. 4

METHOD AND APPARATUS PROVIDING AN ONGOING AND REAL TIME INDICATOR FOR SURVIVAL AND MAJOR MEDICAL EVENTS

CROSS-REFERENCE TO RELATED APPLICATIONS

This application claims priority to U.S. Provisional Application Ser. No. 62/861,788, filed Jun. 14, 2019, the entire contents of which are incorporated herein by reference.

TECHNICAL FIELD OF THE INVENTION

The present invention relates in general to the field of methods and devices for providing an ongoing and real time indicator for prediction of survival and major medical events.

STATEMENT OF FEDERALLY FUNDED RESEARCH

None.

BACKGROUND OF THE INVENTION

Without limiting the scope of the invention, its background is described in connection with monitoring.

Today many different methods are available for providing a myriad of combinations of healthcare. As is well known, most of the healthcare expenditures occur in a transitional state from healthcare to homecare.

In between those two points, healthcare is relatively expensive. During this period of healthcare transition, most patients require increased healthcare in order to either improve the quality of life or extend life. In many cases, the patient is admitted to a hospital for a particular condition and is released to either outpatient in-home care or to assisted-living, or hospice.

In the case of in-home care or assisted living, there is a great need to monitor the patient for activity levels to ensure that they are adequately moving around and are performing most daily activities such as eating, going to the restroom, and or other appropriate activities.

Part of the problem is that there is no easy method to monitor their activity. Most activity monitoring is done either with video cameras or in home archaic care assistance or other such inferior methods.

These monitoring methods can be time-consuming, and in the case of the video system, the caretaker would need to daily and hourly monitor and watch the videos to make sure that the patient is moving around as expected.

What is needed is a method and apparatus to provide caregivers a continuous monitoring indicator for the individual health status and activities and thereby avoiding possible deteriorating and life-threatening situations or conditions.

SUMMARY OF THE INVENTION

The present invention includes a method and apparatus to provide an indicator for each patient such that the caregivers will be able to provide more individual attention to the health status and possibly avoiding possible health deterioration or life-threatening situations.

The patient is provided a wearable watch. This device may contain accelerometers, blood pressure monitors, thermal monitoring, Bluetooth or Wi-Fi capability, and many other methods to monitor the patient's vitals. However, in this case we have provided a capability to individually monitor on a real-time basis using the wearable, the seniors activity level which will provide much more information to the healthcare provider.

In one embodiment, the present invention includes a method for providing an ongoing and real time indicator for predicting remaining lifetimes or risk of health deterioration for one or more patients comprising: providing a monitoring system connected to the cloud, a Wi-Fi or Bluetooth network which is connected to a wearable device; and providing a wearable device which contains one or more accelerometers, temperature monitoring devices, EKG monitoring devices and other useful devices; wherein the wearable device is powered internally by a battery or other such appropriate energy sources. In one aspect, the method further comprises defining the energy difference as daytime energy minus nighttime energy. In one aspect, the method further comprises defining the day and night active percentage differences as the change in daytime activity level percentage minus the change in nighttime activity percentage. In one aspect, the method further comprises defining the net daytime active percentage level as the daytime activity percentage minus the daytime resting percentage. In one aspect, the method further comprises providing sliding windows for any number of consecutive seconds, minutes, hours, days, week, two weeks, months, or years and any other combination or sub division of these time periods. In one aspect, the method further comprises optimizing the correlation coefficient R squared and slope using different time sampling windows and/or data distribution sampling rates. In one aspect, the method further comprises using the slope and r2 value from linear regression model are being updated weekly, and the final slope and r2 value for data analysis will be obtained after the third week cycled. In one aspect, the method further comprises providing sliding windows for any number of consecutive sub seconds two weeks, months, or years and any other combination or sub division of these time periods. In one aspect, the method further comprises optimizing the correlation coefficient R squared value (or adjusted R-squared value) and slope using different sampling windows and/or data sampling rates.

In one embodiment, the present invention includes a device comprising: accelerometers for one gravity (1G), two gravity (2G) and three gravity (3G) measurement capabilities; wherein the accelerometers are capable to monitoring in any continuous time basis from the sub millisecond or microsecond range up to days weeks or months or more; and apply a sliding or moving window from sub seconds to days or weeks or months or more, and to apply calculations to the raw data generated by the accelerometers; having an ability to monitor day, night, activity levels of the patient; and an ability to monitor little to no day, night activity levels of the patient. In one aspect, the device is capable of transmitting the moving window data from microseconds increments to days or weeks or months to the cloud or the Wi-Fi or Bluetooth device containing storage of the raw or time-stamped data. In another aspect, the device is capable of timestamping the data in any incremental size as needed. In another aspect, the device is capable of calculating activity levels such as daytime active percentage, daytime resting percentage, nighttime active percentage, and nighttime resting percentage. In another aspect, the device is capable of providing and measure daytime energy levels and nighttime energy levels. In another aspect, the device is capable of providing high daytime and low night time resting energy levels, resting percentage of daytime energy, high day time percentage levels and low daytime resting percentage, Low night time active percentage levels, activity or movement percentage levels, absolute moving percentage levels, R squared and negative slope Night time energy level increase, daytime activity percentage, nighttime activity percentage, the intersection of any and all of either energy levels or percentage levels, the daytime or nighttime active percentage levels going below the 0% level, the high daytime activity percentage levels plus low day time resting levels, low nighttime active percentage+high nighttime percentage resting levels. In another aspect, the device is capable of defining morning, noon, night or any other such definition and description of a particular energy level time period. In another aspect, the is capable of defining the energy difference as daytime energy minus nighttime energy. In another aspect, the device is capable of defining the day and night active percentage differences as the change in daytime activity level percentage minus the change in nighttime activity percentage. In another aspect, the device is capable of defining the net daytime active percentage level as the daytime activity percentage minus the daytime resting percentage. In another aspect, the device is capable of providing sliding windows for any number of consecutive sub seconds two weeks, months, or years and any other combination or sub division of these time periods. In another aspect, the device is capable of optimizing the correlation coefficient R squared and slope using different sampling windows and/or data sampling rates. In another aspect, the device is able to use exponential, linear regression, moving averages of any type and sampling rates of any type and the usage of any of the regression and moving averages to provide additional analyzable results. In another aspect, the device is capable of recalling any of the fit algorithms and or sampling size to apply as the optimum solution for the sampled data set from the accelerometers. In another aspect, the device is capable of using the combinations of any of the above plus other such capabilities to predict the deterioration or survival.

In another embodiment, the present invention also includes an apparatus for providing an ongoing in real-time indicator for prediction of a use for a lifetime for the patient comprising: providing an ongoing and real time indicator for predicting remaining lifetimes for one or more patients comprising: providing a monitoring system connected to the cloud, a Wi-Fi or Bluetooth network which is connected to a wearable device; and providing a wearable device which contains one or more accelerometers, temperature monitoring devices, EKG monitoring devices and other useful devices; wherein the wearable device is powered internally by a battery or other such appropriate energy sources.

In another embodiment, the present invention includes a method for providing an ongoing in real-time indicator to determine a time interval and duration for predicting a change of an active and a resting phase in patients comprising: sampling a time duration of the active and the resting phase of a patient recursively for various time intervals of 1 h to Nth hour and time duration of N hour to N+1 hour to obtain active and resting phase data; using an eXtreme Gradient Boosting (XGBoost) algorithm on the active and resting phase data to convert weak learners to stronger learners using learners trained against a predictive model; training the model for a maximum time duration and a time interval sufficient to predict a significant change in the activity of the active and the resting phase of a patient; and triggering an alarm when the activity measured for the active and resting phase data drops<50% from a critical level. In one aspect, setting an alarm level based on a change in a phase exchange of an active and a resting phase in which the signals overlap. In another aspect, the active and resting phase data were unnormalized. In another aspect, the algorithm operates without generating independent dummy variables. In another aspect, one or more pre-computed categories are used to avoid a random split of the tree for selection of variables, and the active and resting phase data was used as split point prior to performing the classification into categories.

In another embodiment, the present invention includes a non-transitory computer readable medium for providing an ongoing and real time indicator for predicting remaining lifetimes for one or more patients, comprising instructions stored thereon, that when executed by a computer having a communications interface, one or more databases and one or more processors communicably coupled to the interface and one or more databases, perform the steps comprising: providing a monitoring system connected to the cloud, a Wi-Fi or Bluetooth network which is connected to a wearable device; and providing a wearable device which contains one or more accelerometers, temperature monitoring devices, EKG monitoring devices and other useful devices; wherein the wearable device is powered internally by a battery or other such appropriate energy sources.

In another embodiment, the present invention includes an apparatus for providing an ongoing and real time indicator for predicting remaining lifetimes for one or more patients comprising: a device that samples a time duration of the active and the resting phase of a patient recursively for various time intervals of 1 h to Nth hour and time duration of N hour to N+1 hour to obtain an active and resting phase data; a processor comprising a non-transitory computer readable medium connected or connectable to the device to provide an ongoing and real time indicator for predicting remaining lifetimes for one or more patients, comprising instructions stored thereon, that when executed by a computer having a communications interface, one or more databases and one or more processors communicably coupled to the interface and one or more databases, perform the steps comprising: using an eXtreme Gradient Boosting (XGBoost) algorithm on the active and resting phase data to convert weak learners to stronger learners using learners trained against a predictive model; training the model for a maximum time duration and a time interval sufficient to predict a significant change in the activity of the active and the resting phase of a patient; and triggering an alarm when the activity measured for the active and resting phase data drops<50% from a critical level. In one aspect, setting an alarm level is based on a change in a phase exchange of an active and a resting phase in which the signals overlap. In another aspect, setting the alarm level is based on a change in a phase exchange of an active and a resting phase in which the signals overlap. In another aspect, the active and resting phase data were unnormalized. In another aspect, the algorithm operates without generating independent dummy variables. In another aspect, one, two, three, or more pre-computed categories are used to avoid a random split of the tree for selection of variables, and the active and resting phase data was used as split point prior to performing the classification into categories.

BRIEF DESCRIPTION OF THE DRAWINGS

For a more complete understanding of the features and advantages of the present invention, reference is now made to the detailed description of the invention along with the accompanying figures and in which:

FIG. 1. Metrics of three methods.

FIG. 2. Procedures of energy level analysis.

FIG. 3a. Procedures for calculating a daytime active percentage and daytime resting percentage.

FIG. 3b. Procedures for calculating a nighttime active percentage and nighttime resting percentage.

DETAILED DESCRIPTION OF THE INVENTION

Figure 4:
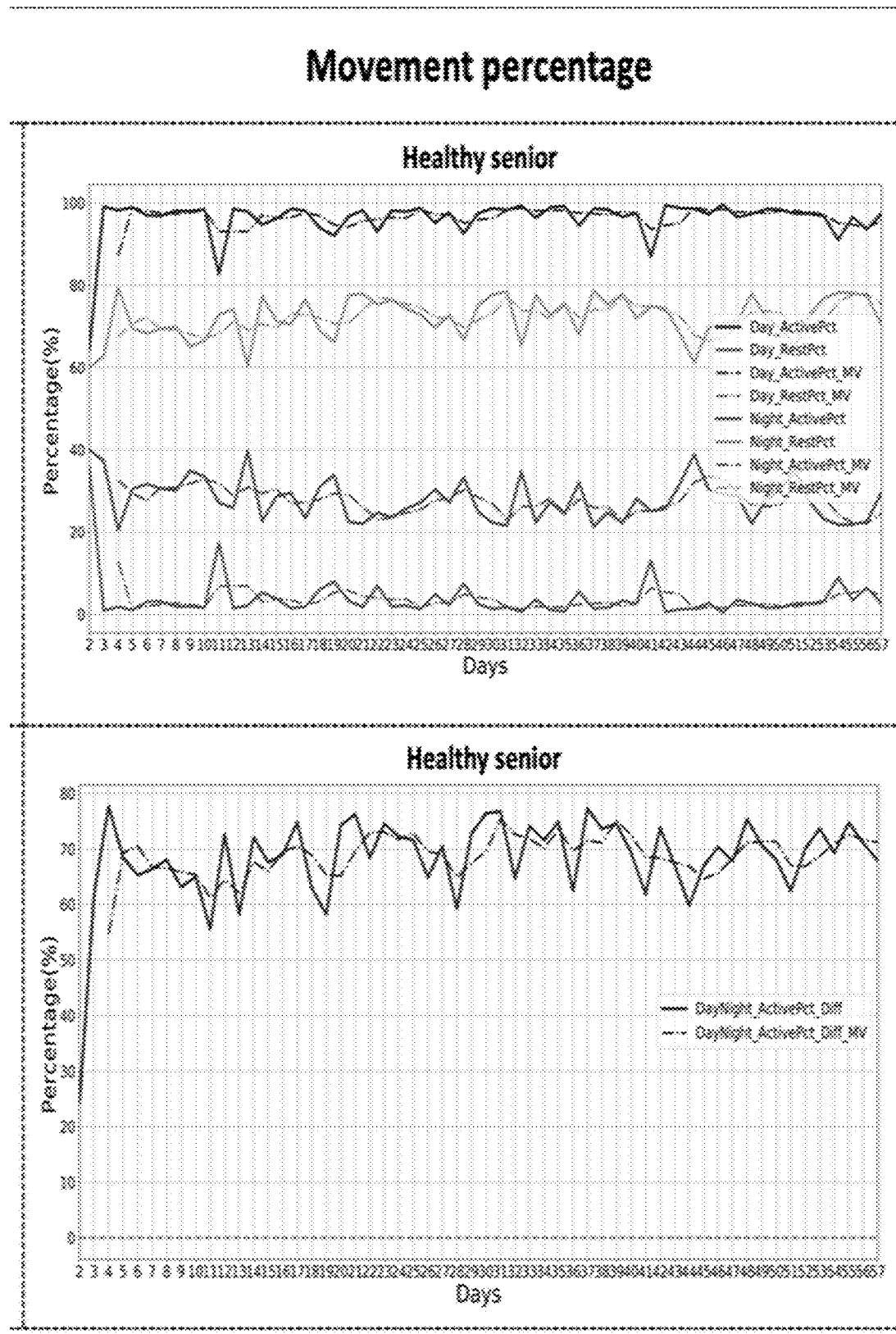
FIG. 4. Figures for typical healthy person using both energy level and movement percentage approaches.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not limit the invention, except as outlined in the claims.

Today, the patient who has endured a medical condition may either enter the hospital or resides in an assisted living home. Both environments are usually served by many healthcare professionals; however these professionals may or may not have the time or energy to provide the individual attention needed to monitor the daily activities of the patient. Today, most healthcare professionals make rounds to each room to ensure that the patient is OK; however, the care giver may or may not see the patient or remember the appropriate activity levels and/or the appropriate daily activity of the patient. Most professionals are too busy to provide organized and regular systematic personal care for each and every patient. As used herein, a major medical event refers to a life-threatening event, or an event that will cause significant, long-term morbidity or mortality, such as a fall that would cause one or more broken bones, significant bruising, damage to soft tissue such as a partial or total lung collapse, concussions, damage to major muscles, heart disease, cardiovascular disease, high blood pressure, and the like.

The present invention includes a method and apparatus to provide an indicator for each patient such that the caregivers will be able to provide more individual attention to the patients' health status and possibly avoiding possible life-threatening situations. In one example, the patients are seniors, e.g., having an age greater that 60, 65, 70, 75, 80, 85 or 90 years old.

The patient is provided a wearable watch. This device may contain accelerometers, blood pressure monitors, thermal monitoring, Bluetooth or Wi-Fi capability, and many other methods to monitor the patient's vitals. However, in this case we have provided a capability to individually monitor on a real-time basis using the wearable, the individual activity level which will provide much more information to the healthcare provider.

In this particular testing, we monitored 11 residents around 500 person days including three deceased residents and healthy patients' residence all over a span of a four-month observation period.

One method uses the energy level that includes daytime and nighttime energy levels to monitor the daytime activity and nighttime activity. Another method uses movement percentage that includes daytime active percentage, daytime resting percentage, nighttime active percentage, and nighttime resting percentage.

High daytime activity percentage plus low daytime resting percentage yield in very active in the daytime. Low nighttime active percentage plus high nighttime resting percentage yield in very good sleep at night.

The key parameter differences between energy level approach and movement percentage approaches are provided. The key parameter is the method using energy levels for different deceased and healthy patients whereby the energy level was provided as momentum as mV2 where m is mass and V is velocity. The watch contained accelerometers which provide 1G, 2G, and 3G counts on a regular basis.

Method three uses a concept of zero movement which can be derived from the incremental counts of 1G, 2G and 3G to create a resting percentage in the daytime and night time respectively.

Zero movement happens when 1G counts equals more'2G counts which equals more 3G counts which all equals zero. In other words, zero movement can be defined by the zero summation of counts of 1G 2G and 3G.

The resting percentage are calculated by those counts and the active percentage is equal to 100% minus the resting percentage.

FIG. 1 shows the results and/or metrics of the three methods and the mnemonic definitions of the parameters are contained at the bottom of each figure. Three methods are shown.

Energy level approach provides the best results whereas daily movement percentage shows low-level accuracy, precision, and specificity by using daily active/resting percentage only. However, dividing the daily active percentage into daytime and nighttime active percentage and dividing the daily resting percentage into daytime and nighttime resting percentage improves accuracy, precision, and specificity.

Referring to FIG. 2, the input parameters are defined using the energy level and M*Vsquared. The procedure is outlined in the FIG. 2. In all subsequent cases the energy levels are monitored throughout the day and night.

In the case of method two a seven-day sample moving average is calculated from the daily energy difference and a linear regression model is used to predict the results. Different screening levels are used as well.

Referring to FIG. 3 the input parameters differed by using additional 1G to G and 3G measurements every five minutes and the procedure consisted of measuring the total count plus incremental 1G to G and 3G measurements. If there was no movement the summation would increment the zero count by one. Thus, the 1G/2G/3G computation equals zero. Compute the total number of zeros and total count within the daytime.

And calculating a daytime active percentage and daytime resting percentage as indicated in FIG. 3a. FIG. 3b involves using method three in the night time where the total count is incremented by one and measuring the 1G 2G and 3G counts and again if the summation of each of the 1/2/3G counts is equal to 0 counts then increment by one the total number of zeros.

The totaled count (1/2/3G) are being used to calculate nighttime active percentage and nighttime resting percentage.

However, in this case a three-day moving average is calculated for these parameters. The intersection of the daytime activity percentage and the nighttime active percentage is used to recognize for the unhealthy patients and also attempt to monitor the trend for those patients which will soon decease.

FIG. 4 shows plots for healthy typical person using energy level and movement percentages. Notice that the slopes for the energy levels and energy differences in this particular figures are increasing as a function of time.

Figure 5:
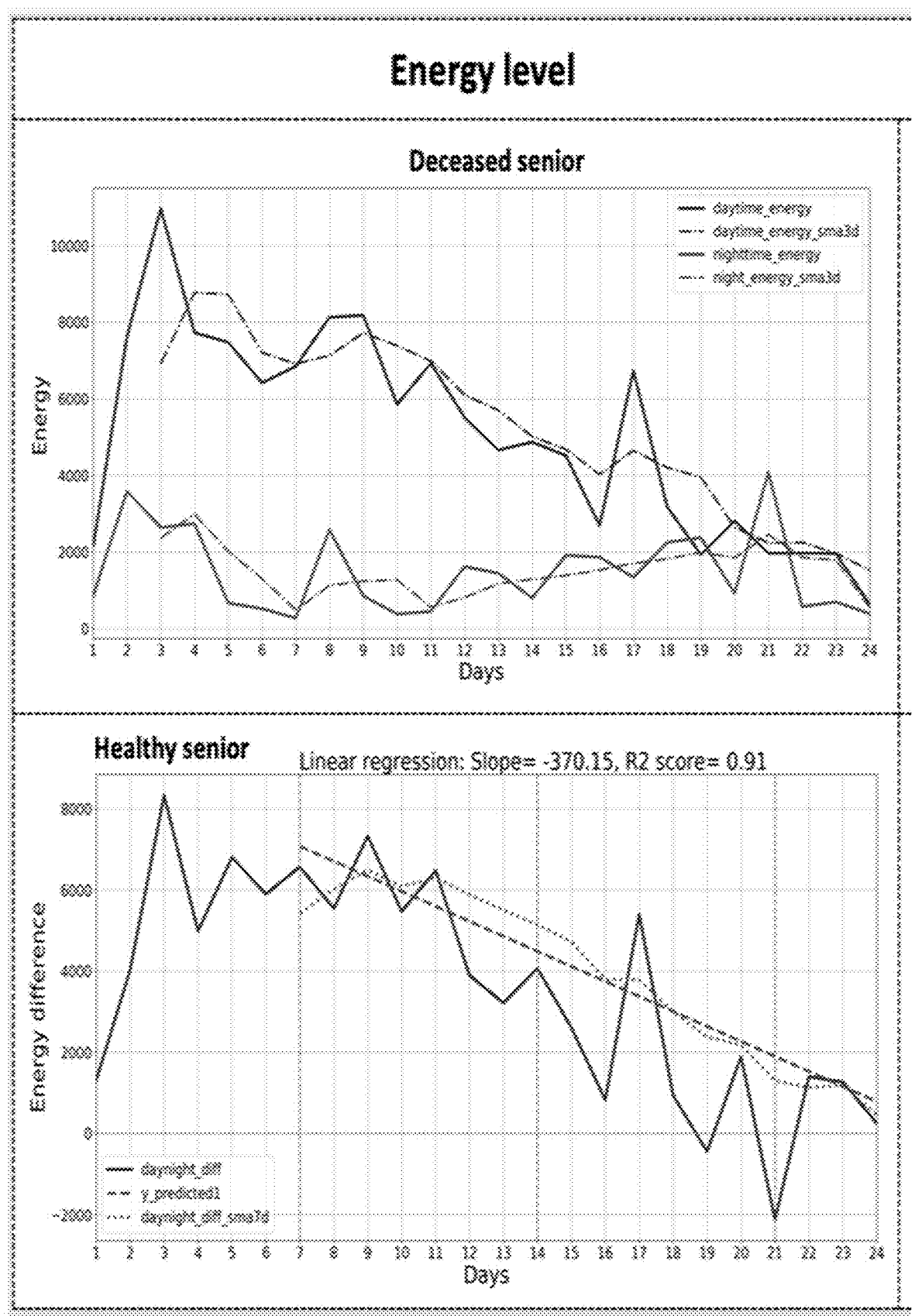
FIG. 5. Figures for a typical deceased person using both energy level and movement percentage approaches.
Figure 5:
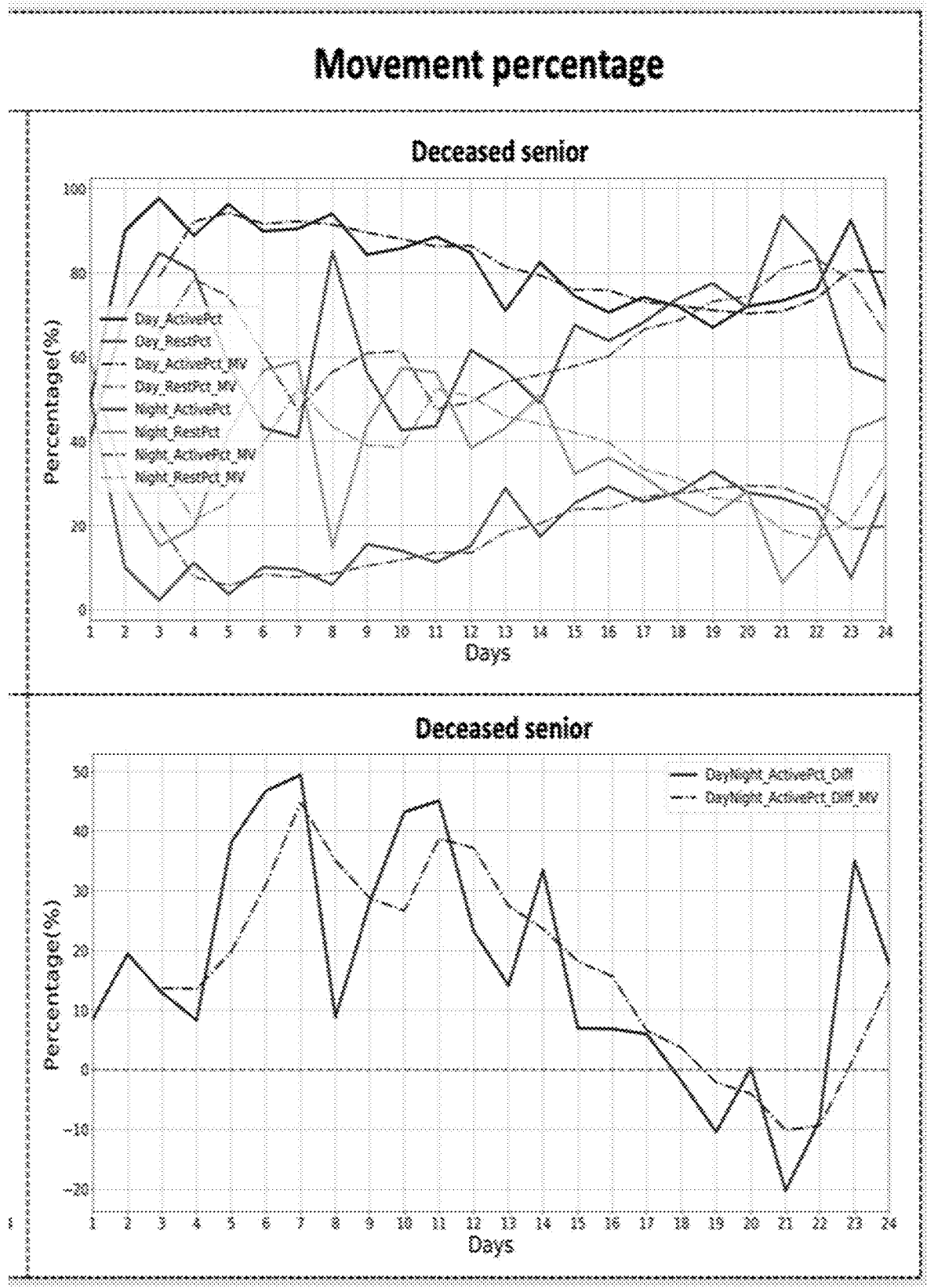
Figure 6:
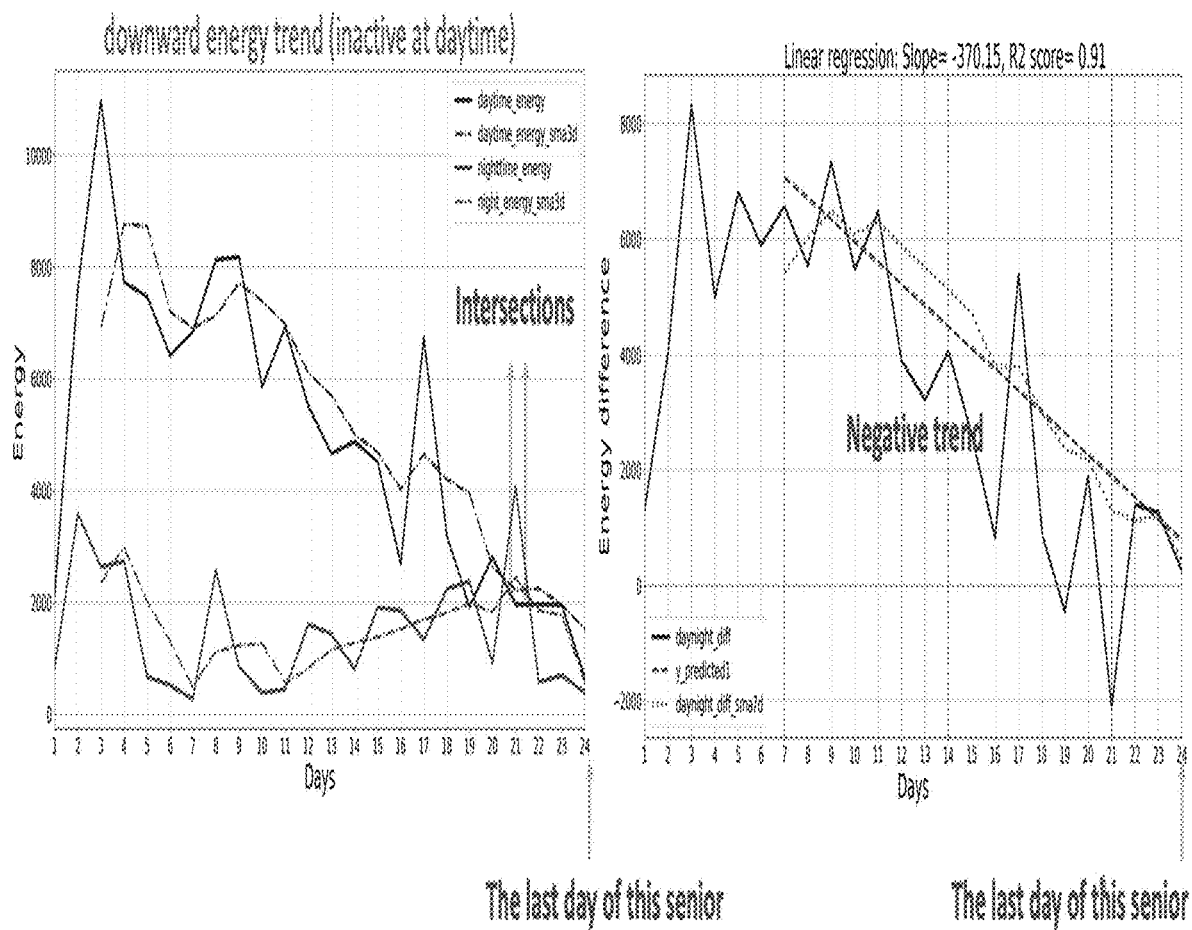
FIG. 6. Figures for typical deceased person using energy level approach.

In movement percentage approach the same applies. And the percentage of the daytime active plot is very high at the seventy percent range. In FIG. 5 we see a plot of a deceased person using both energy level and movement percentages. Note that the slopes are negative and will approach zero at some point. In FIG. 6, the data from a deceased person using energy level approach shows that his/her daytime and nighttime energy level will eventually cross and create intersection(s) near the last day of his/her life.

The energy difference, which is equal to daytime energy level minus nighttime energy level, will eventually approach zero near the last day of his/her life. The linear regression model is being used to calculate the slope and R-squared value (or adjusted R-squared value) and create a predicated line in red color in the right side of the FIG. 6.

Figure 7:
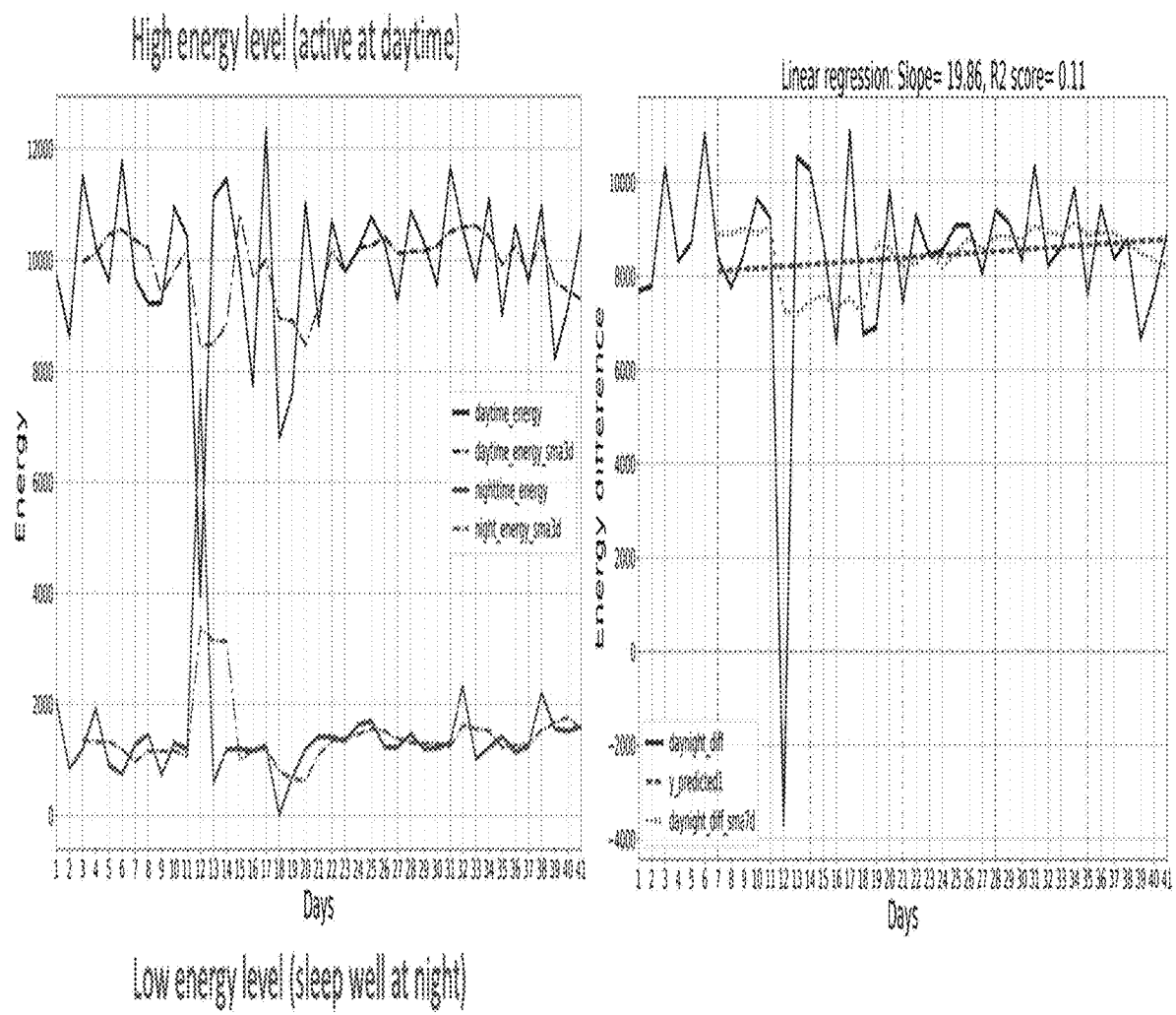
FIG. 7. Figures for healthy deceased person using energy level approach.

FIG. 7 depicts the findings energy level approach for a healthy person. Note that the high energy level in the daytime remains fairly constant at 10,000 energy units and the nighttime energy level is very low at around 2000 energy levels which shows a very high activity in the daytime and good resting at night. In addition, the linear regression model on the right-hand side of FIG. 7 shows a constant high energy difference between the daytime and nighttime.

Figure 8:
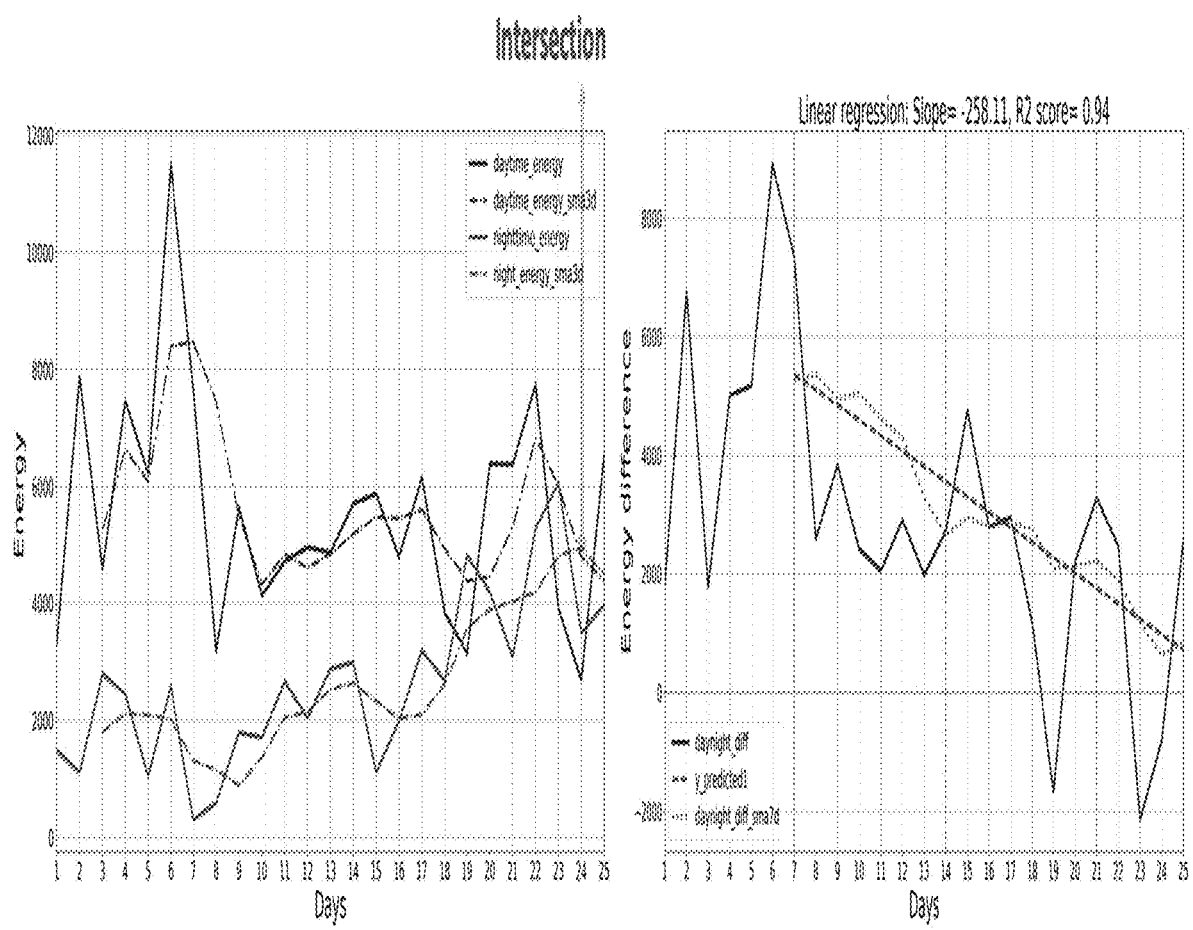
FIG. 8. Figures of typical deceased person using energy level approach.

Furthermore, no intersection can be observed from daytime and nighttime energy level. The mean value of daily energy difference for 8 healthy people (15,664) is much greater than the mean value of daily energy difference for 3 deceased people (2,257). FIG. 8 shows that the nighttime energy levels will tend to increase to the point where the daytime energy level equals a nighttime energy level. This upward nighttime energy trend shows that this person did not sleep well at night near the last day of his/her life. At the point of the crossover, the patient passed away. On the right-hand side of FIG. 8, the predicated line from linear regression model shows that the level of energy difference is decreasing and approaching zero as well.

Figure 9:
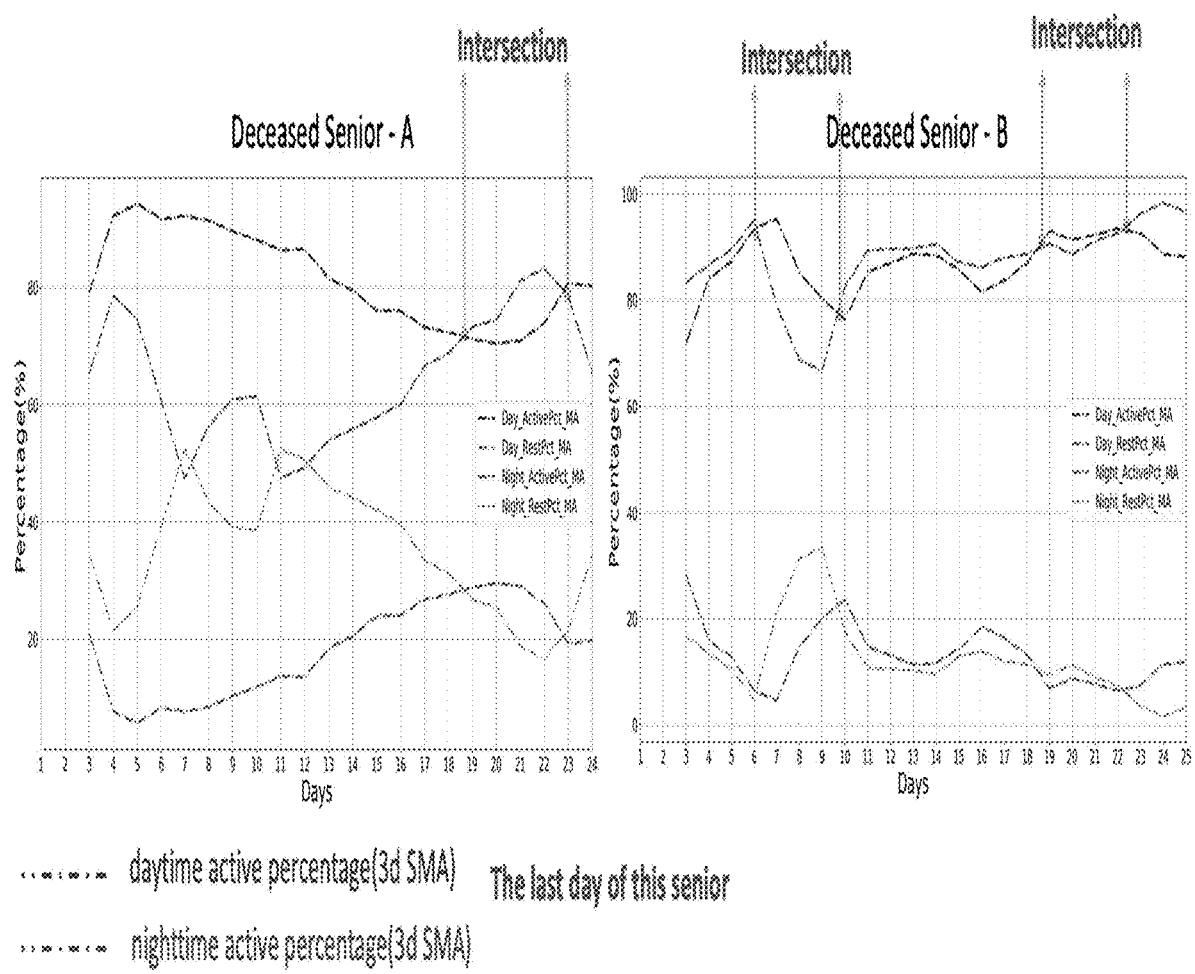
FIG. 9. Figures for typical deceased person using movement percentage approach.

FIG. 9 shows the results from movement percentage approach for the deceased person. In this case, two major parameters including daytime active percentage with 3-day moving average and nighttime active percentage with 3-day moving average were used for recognizing the people who are decaying over time. The daily active percentage and nighttime active percentage shows one or more crossover points and those intersections provide a clue that the patient is not doing well.

Figure 10:
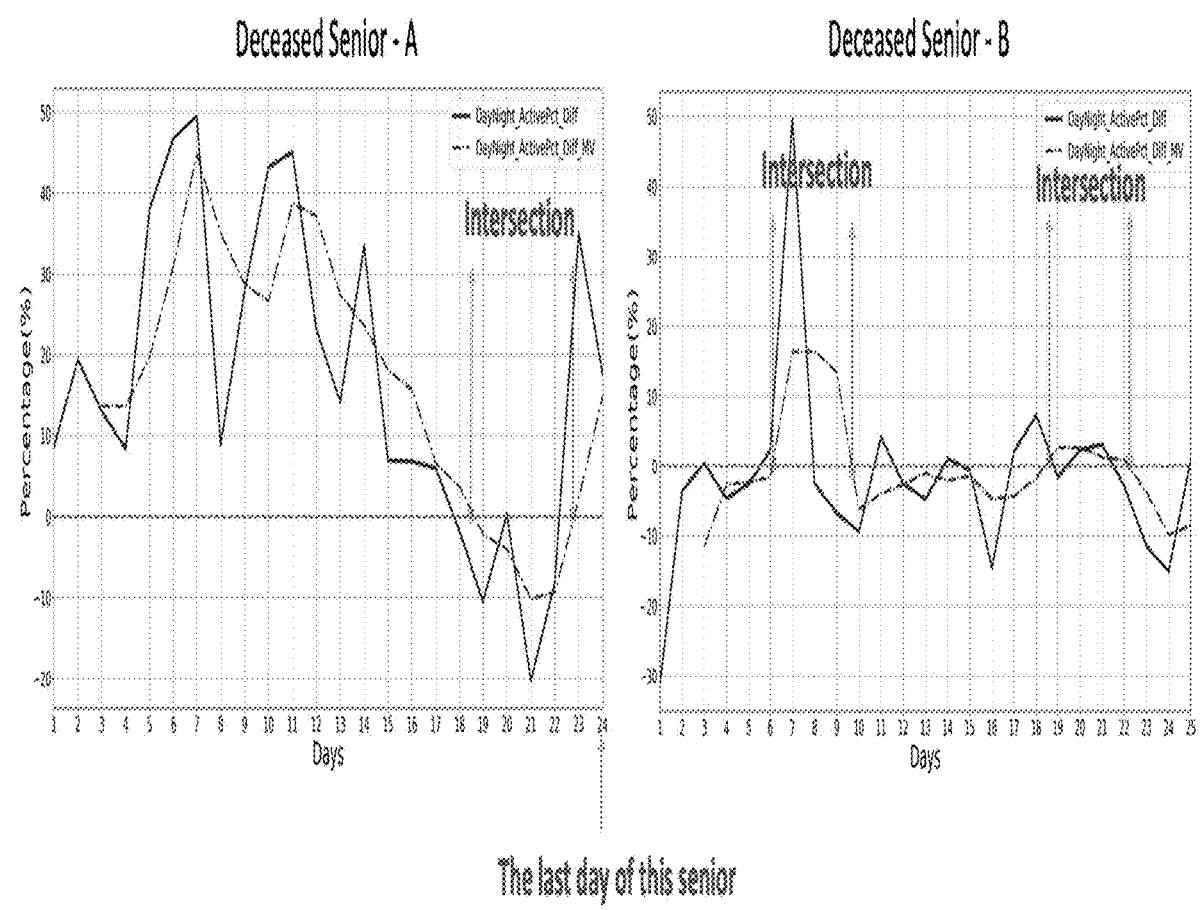
FIG. 10. Figures for typical deceased person using movement percentage approach.
Figure 11:
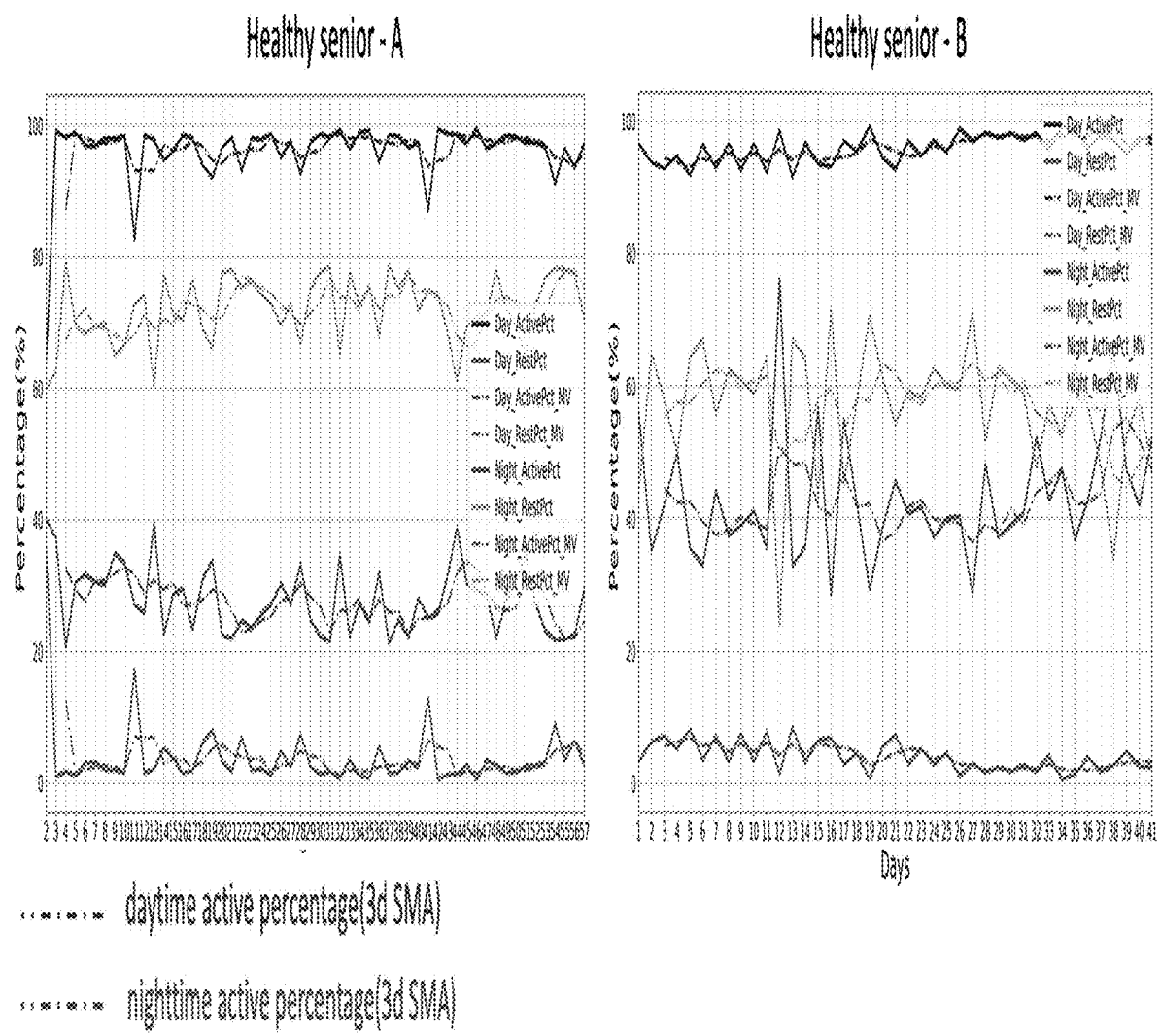
FIG. 11. Figures for typical healthy person using movement percentage approach.
Figure 12:
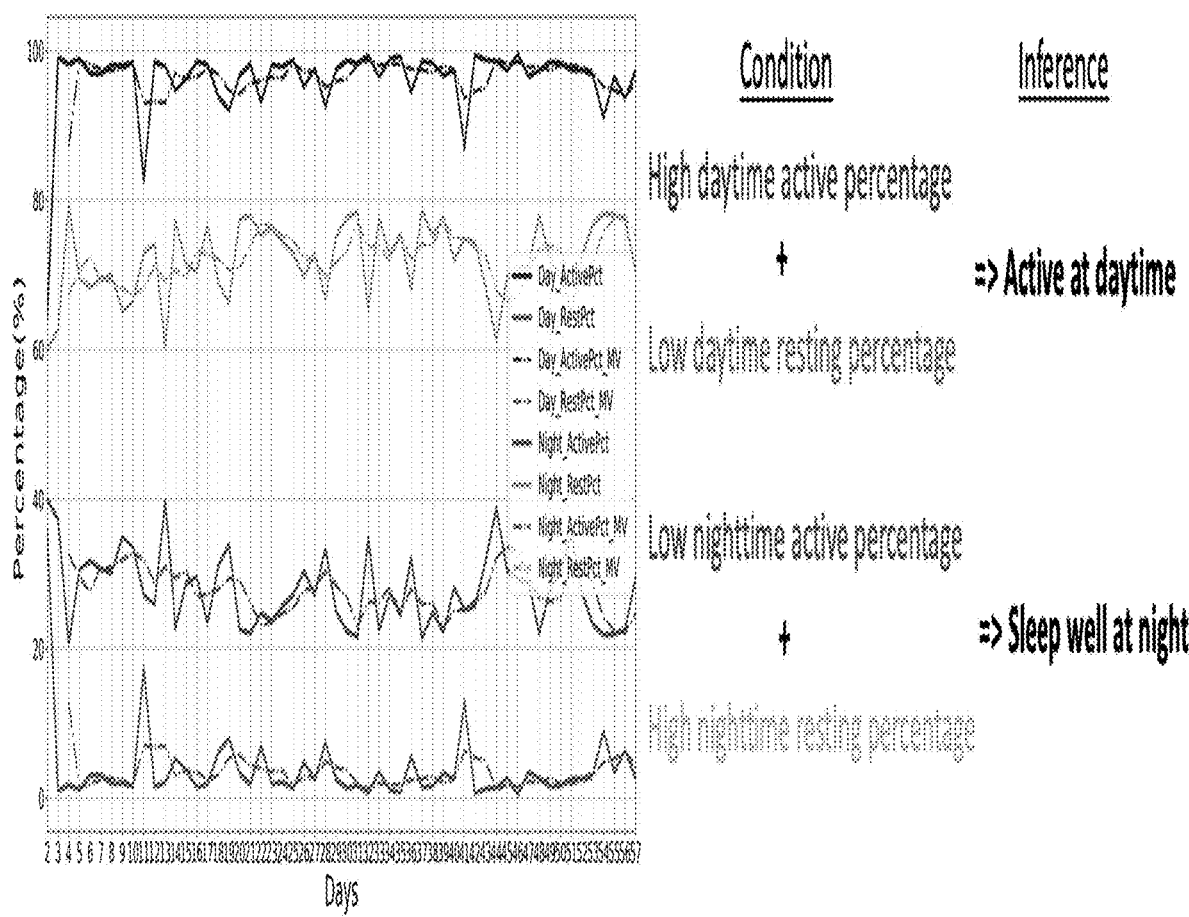
FIG. 12. Figures for typical healthy person using movement percentage approach.

In FIG. 10, the differences between daytime active percentage and nighttime active percentage with a three-day moving average will eventually cross the zero-percentage level and create intersections between the day/night levels for those patients are shown. FIG. 11 shows the findings from movement percentage approach. For healthy people, there is no intersection between the daytime active percentage and Nighttime active percentage. The same is shown in FIG. 12. Where the daytime active percentage is greater than a nighttime active percentage for all healthy people.

Figure 13:
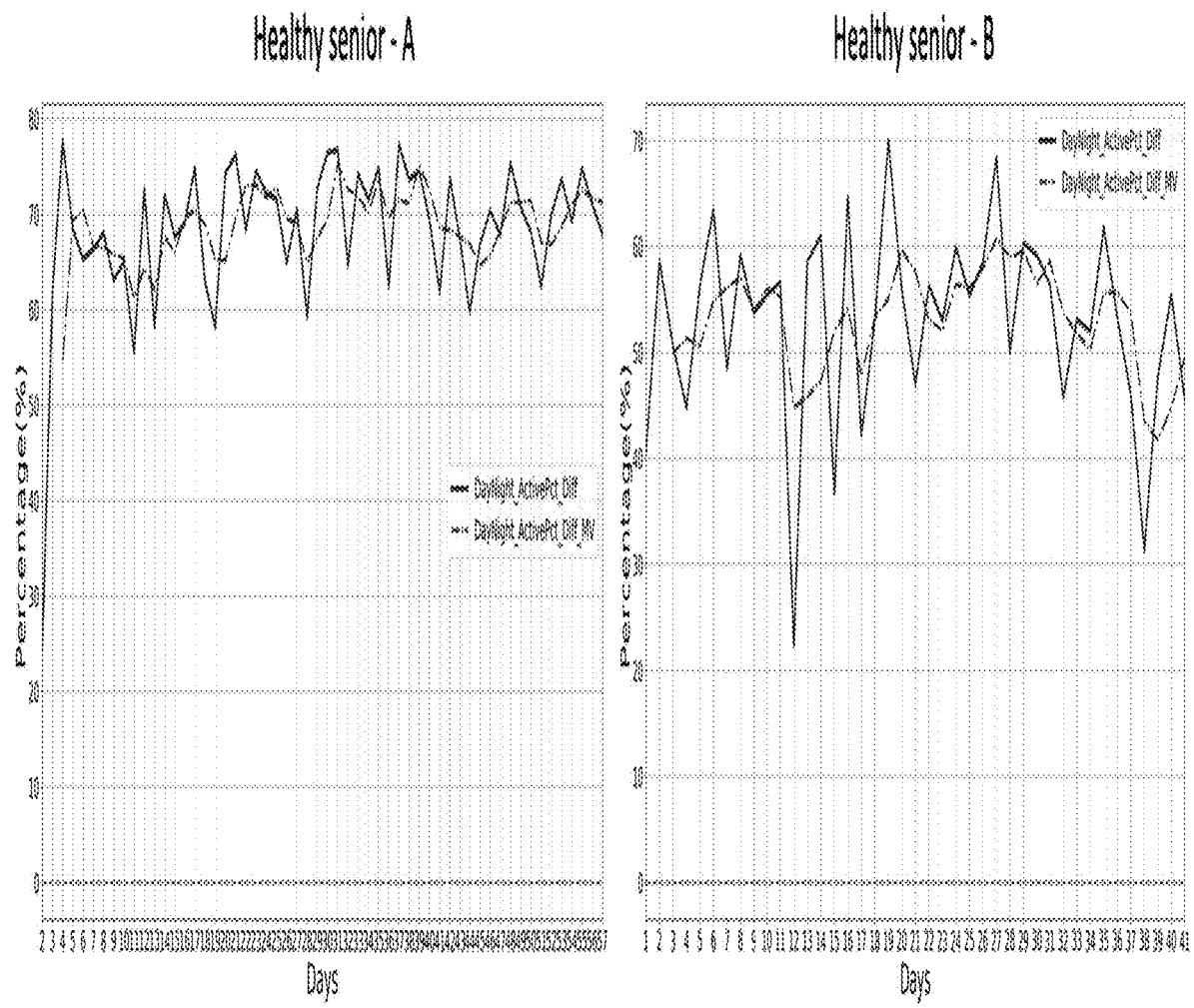
FIG. 13. The differences of day-night active percentage for healthy person.
Figure 14:
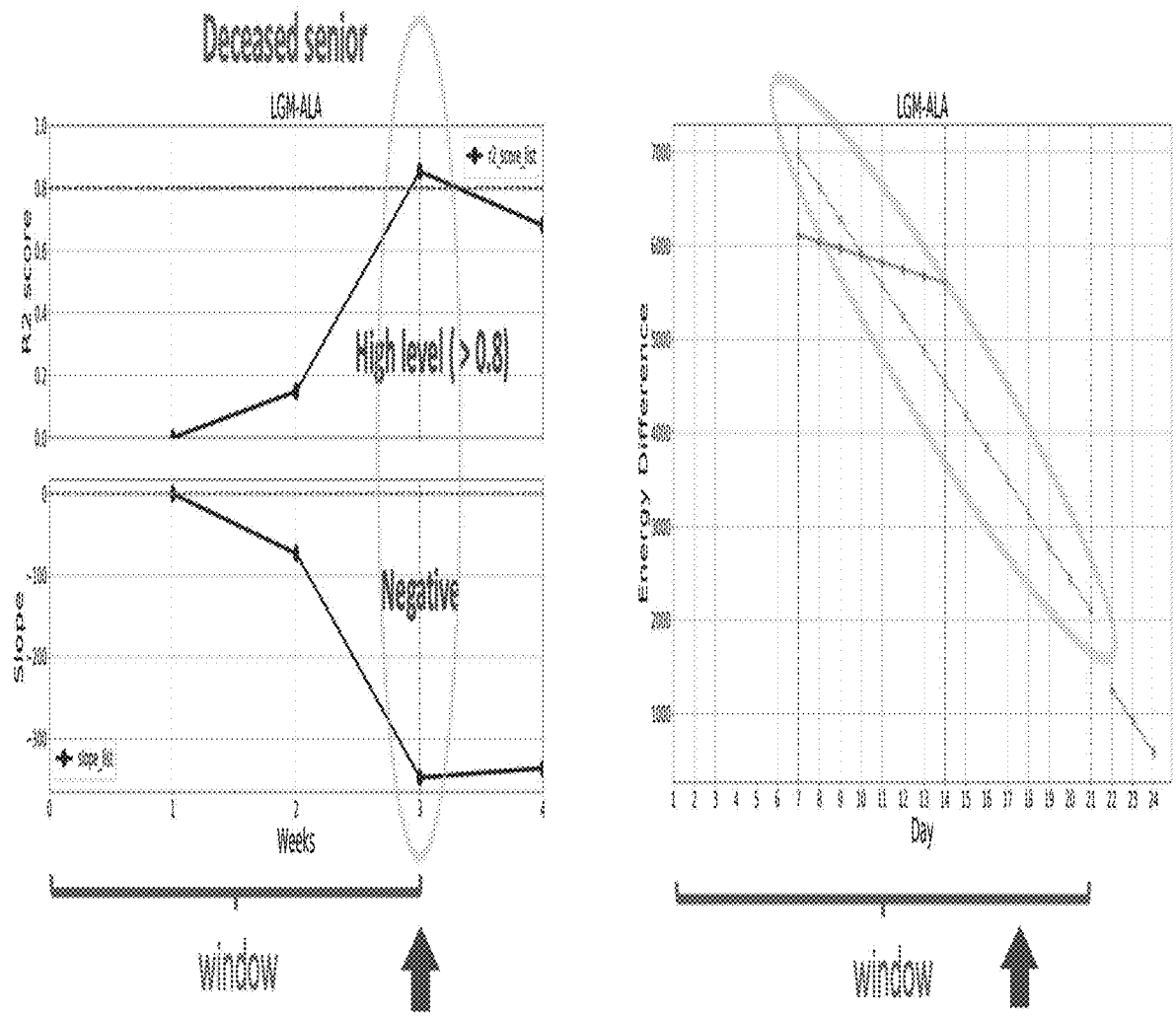
FIG. 14. An updated algorithm of energy level approach that can reduce the bias of slope and r2 value.

FIG. 13 shows that the differences of daytime active percentage and nighttime active percentage will be above the 0% for all healthy people. FIG. 13. The differences of day-night active percentage for healthy people. FIG. 14 shows that reducing the bias of slope and r2 value can be achieved by analyzing three consecutive weeks (window) from method 2.

The present invention also includes one or more of the following:

The slope and r2 value from linear regression model are being updated weekly, and the final slope and r2 value for data analysis will be obtained after the third week cycled in orange (see figures above);

Providing sliding windows for any number of consecutive sub seconds two weeks, months, or years and any other combination or sub division of these time periods; and/or Optimizing the correlation coefficient R squared value (or adjusted R-squared value) and slope using different sampling windows and/or data sampling rates.

The present invention includes a method and apparatus providing a method to identify the critical time point where activity level with minimum time interval and duration can help to identify the alarming change and alert as a real-time mentoring system.

TABLE 1

Abstract observations from daily activity data from people

| Data observations | Observation values | Limitations/Range For observations |
|---|---|---|
| Alive subjects (A) | 72 | 69 subjects used in model building |
| Deceased(D) subjects | 5 | All 5 used in model building |
| Minimum time interval calculated using algorithm for active and resting phase status change. | (Average) 48 minutes | Confidence Interval (CI) [45.8-71] minutes |
| Minimum time duration calculated using algorithm for active and resting phase status change. | (Average) 8.4 hours | Confidence Interval (CI) [6.2-12.9] hours |

Based upon this criticality threshold, the obtained estimated probability is classified namely "Alarming stage" and "Docile stage". Here XGboost algorithm was applied to linear and non-linear models as it works on decision boundary that can be applied linear or non-linear. Polynomial order was increased to get complex decision boundaries and test the boundary limitation of time interval.

After the model learning and sampling of time interval and duration, the point of decline and point of the rise in acting and resting phase were identified starting from a 10% drop.

To develop a robust model, k-fold cross-validation was performed taking all the entries in the training set for both pieces of training as well as validation at each % drop.

Further, the drop was increased to 30,35, 40, 50, and 55% drop in the activity levels. At each level of activity drop, the performance of the model was calculated in terms of sensitivity, specificity, and p-value.

During the model tuning the occurrence of false positives were omitted with relaxed parameters XGBRegressor namely (objective='reg:squarederror', col_sample_bytree=0.4, learning_rate=0.5, max_depth=10, alpha=10, n_estimators=500).

Further, post-initial training of the model using above tuning parameters we obtained minimum time interval of 48 minutes and time duration of 8.4 hours as essential duration to predict the overlap in active and resting phase as shown in Table 1.

Keeping the standard error rate mind the time interval of 60 minutes and a duration of 10 hours will be used in ongoing real-time tracking of the alarming activity phase. The performance of the model on various stages of activity reduction is shown in Table 2.

TABLE 2

Activity phase change and performance of classification model.

| Model | Activity Reduction <30% | Activity Reduction <35% | Activity Reduction <40% | Activity Reduction <50% | Activity Reduction <55% |
|---|---|---|---|---|---|
| Sensitivity | 0.71 | 0.73 | 0.8 | 0.83 | 0.83 |
| Specificity | 0.91 | 0.87 | 0.96 | 0.81 | 0.90 |
| Prevalence | 0.124 | 0.183 | 0.156 | 0.169 | 0.122 |
| Balanced Accuracy | 0.71 | 0.78 | 0.82 | 0.87 | 0.865 |
| P-Value | 0.42 | 0.06 | 0.002 | 0.032 | 0.041 |

As shown in Table 2 it is essential to note that during the activity reduction <35% in many cases the active and resting signal had no overlap. However, in >40% there was overlap observed in active and resting phase.

As shown in Table 2 and our initial cut off of activity reduction (<50%), the overall accuracy of the model is around 87%. Similarly, for activity reduction (<55%), the overall accuracy of the model is around 86.5%.

In conclusion, this is the first real-time activity tracking model based on phase change of activity curve using xgboost algorithm that can identify the minimum time interval and duration, essential % of activity reduction required to alarm, and predict the alarming stage of health in people.

Algorithm Novelty.

The problem of real-time signal tracking to predict the sedentary in people required to have an ensemble algorithm that can allow combining models to get the activity and time identification task done. However, despite the ensemble nature of xgboost, it lacked the following points that were modified to achieve the in-activity signal identification.

Continuous signal: xgboost works well with non-categorical data however, in the current case various stages of signals with the certainty of upcoming signal had defined categories. However, the other good nature of tree-based algorithms and in this case xgboost is that it does not require the normalization of signals. However, SVM (Support vector machine), a widely used algorithm require to normalize the features and that changes the scale of deviation in signals and thus not fit for time interval and duration identification.

Realizing that, the inventors, decided to use xgboost where unnormalized signals can be used, and then modified the algorithm for categorical analysis.

In the modification of algorithm while splitting the data into trees, unlike the original behavior of the algorithm, where it generates independent dummy variables to define the category and thus compromised with purity.

In these modification, the inventors pre-computed the required number of categories based on three levels of 1G, 2G, and 3G. This avoided the random split of the tree for the variable selection, and used activity levels as split point and then performed the classification.

By doing so, the inventors avoided the black-box nature of the algorithm, and also the chance of false-positive occurrence, essential to the application used herein.

This change of tree splitting strategy and category refinement required to alter the running and boosting of the algorithm to retain its original quality of dealing for unnormalized data. As signals can have steep changes essential to track the activity and cannot be captured if normalized.

To changes in Tuning and Boosting are as given below:

Tuning: The already existing tuning paraments of the algorithm requires to have 3 mandatory inputs a) depth of tree b) the number of tree c) shrinkage parameter.

In the current use case tuning was required while identifying the minimum duration and interval required to predict the activity change. On a large time point, the default tuning algorithm worked well with our optimized xgboost. However, for a shorter duration of 8.4 days and 48 minutes, there were higher chances to get false positives. Thus, the inventors designed the tuning of the algorithm based on learning on bigger time points and intervals. In every iteration with given time duration and time interval, the tuning paraments used were obtained.

The following parameters were used for tuning: (a) Total no of the tree for maximum time interval- Total no of tree used for each category split)b) signal intensity difference during that interval (viz: difference in maximum-minimum energy levels).

Thus, the inventors developed a more optimal tuning approach than traditional one for categorical signal data.

Analysis Novelty

Using minimum time duration and interval of sedentary stage identification

Personalized activity %, that can be alarming for the person's health

Procedures:

1. Compute daily daytime total energy and nighttime total energy 2. 1st pass:

Calculate moving average for maximum no of days available for each subject

Apply iterative learning through sequential reduction time duration (D) and time interval (T).

For each subset of <D, T>, relearning the model and obtain the performance of model.

3. Track the decline and the overlap of active and resting phase curves in deceased people.

4. Obtain energy time difference of each subset of <D, T> (day time energy -night time energy)

5. Calculate moving average of each <D, T> pair.

6. Identify the <D, T> pair to be used for prediction of activity reduction.

Apply xgboost model for activity tracking and reduction in healthy person's real time.

Output: Sensitivity, specificity, intercept slope with actual and anticipated change in activity 88. 2nd pass: Distinguish healthy and deceased person based on obtained <D, T> pair.

9. 3rd pass: classify the healthy people into "complete healthy" and "alarming stage" using R-squared mean value from model.

To identify the most optimal minimum time of prediction of sedentary individuals it is essential to look at the smallest unit of time interval starting from 1 second to maximum time of the individual's total activity. Post sampling of the time intervals, the maximum and minimum time points referred to as maximum and minima of activity time can be compared again to each time point. More formally if time point is denoted by t, and the overall duration is divided in the fraction oft1 to t(n−1) where n is the maximum time in seconds. Now, if active Phase is A and resting phase is R, then a combination of activity can be <A, R>. Then to calculate the timepoint of convergence to different intervals and intervals with the minimum duration that defines the trajectory change of A and R can be used as the time for triggering the alarm. The method can use all possible subject intervals and provide the most accurate minimum time duration and interval to predict sedentarily. Thus, the above methods can also include: (1) Sampling intervals where the trajectory of resting and active phase crosses and personalized alarming system for each subject; and/or (2) the identification of a minimum time for each subject that leads to subject-specific sedentary analysis and decisions or suggestions based on pre-determined treatments or interventions.

In one embodiment, the present invention includes a method for providing an ongoing and real time indicator for predicting remaining lifetimes for one or more patients comprising, consisting essentially of, or consisting of: providing a monitoring system connected to the cloud, a Wi-Fi or Bluetooth network which is connected to a wearable device; and providing a wearable device which contains one or more accelerometers, temperature monitoring devices, EKG monitoring devices and other useful devices; wherein the wearable device is powered internally by a battery or other such appropriate energy sources.

In one embodiment, the present invention includes a device comprising, consisting essentially of, or consisting of: accelerometers for one gravity (1G), two gravity (2G) and three gravity (3G) measurement capabilities; wherein the accelerometers are capable to monitoring in any continuous time basis from the sub millisecond or microsecond range up to days weeks or months or more; and apply a sliding or moving window from sub seconds to days or weeks or months or more, and to apply calculations to the raw data generated by the accelerometers; having an ability to monitor day, night, activity levels of the patient; and an ability to monitor little to no day, night activity levels of the patient. In another embodiment, the present invention also includes an apparatus for providing an ongoing in real-time indicator for prediction of a use for a lifetime for the person comprising, consisting essentially of, or consisting of: providing an ongoing and real time indicator for predicting remaining lifetimes for one or more patients comprising: providing a monitoring system connected to the cloud, a Wi-Fi or Bluetooth network which is connected to a wearable device; and providing a wearable device which contains one or more accelerometers, temperature monitoring devices, EKG monitoring devices and other useful devices; wherein the wearable device is powered internally by a battery or other such appropriate energy sources.

In another embodiment, the present invention includes a method for providing an ongoing in real-time indicator to determine a time interval and duration for predicting a change of an active and a resting phase in patients comprising, consisting essentially of, or consisting of: sampling a time duration of the active and the resting phase of patient recursively for various time intervals of 1 h to Nth hour and time duration of N hour to N+1 hour to obtain active and resting phase data; using an eXtreme Gradient Boosting (XGBoost) algorithm on the active and resting phase data to convert weak learners to stronger learners using learners trained against a predictive model; training the model for a maximum time duration and a time interval sufficient to predict a significant change in the activity of the active and the resting phase of the patient; and triggering an alarm when the activity measured for the active and resting phase data drops<50% from a critical level. In another embodiment, the present invention includes a non-transitory computer readable medium for providing an ongoing and real time indicator for predicting remaining lifetimes for one or more patients, comprising instructions stored thereon, that when executed by a computer having a communications interface, one or more databases and one or more processors communicably coupled to the interface and one or more databases, perform the steps comprising, consisting essentially of, or consisting of: providing a monitoring system connected to the cloud, a Wi-Fi or Bluetooth network which is connected to a wearable device; and providing a wearable device which contains one or more accelerometers, temperature monitoring devices, EKG monitoring devices and other useful devices; wherein the wearable device is powered internally by a battery or other such appropriate energy sources.

In another embodiment, the present invention includes an apparatus for providing an ongoing and real time indicator for predicting remaining lifetimes for one or more patients comprising, consisting essentially of, or consisting of: a device that samples a time duration of the active and the resting phase of patient recursively for various time intervals of 1 h to Nth hour and time duration of N hour to N+1 hour to obtain an active and resting phase data; a processor comprising a non-transitory computer readable medium connected or connectable to the device to provide an ongoing and real time indicator for predicting remaining lifetimes for one or more patients, comprising instructions stored thereon, that when executed by a computer having a communications interface, one or more databases and one or more processors communicably coupled to the interface and one or more databases, perform the steps comprising: using an eXtreme Gradient Boosting (XGBoost) algorithm on the active and resting phase data to convert weak learners to stronger learners using learners trained against a predictive model; training the model for a maximum time duration and a time interval sufficient to predict a significant change in the activity of the active and the resting phase of the patient; and triggering an alarm when the activity measured for the active and resting phase data drops<50% from a critical level.

Further, when the alarm is triggered, the present invention also provides providing a treatment selected from: waking up the subject, diagnosing the subject, resuscitation, administration of a medication, administration of a remedy, administration of a nutritional supplement, administration of a vitamin, exercise, physical therapy, massage, stretching, consumption of food, rest, sleep, and any combination thereof. The software can provide a pre-selected series or a flow-chart of interventions based on the data analysis and triggering of the alarm.

In another embodiment, the present invention uses sample intervals at different time interval values and as the sample interval values are being measured, they are compared against any short term intervals to longer-term intervals, which are used to predict the trajectory of the activity levels. Thus, the machine is learning through convergence by convolving all sample intervals over time. By convolving all sample intervals over time it provides multiple different weighted sample intervals which help produce better confidence intervals and better trajectory predictions because there are many more voting samples working over different time intervals instead of only one biter. This is in contrast to what typical algorithms use, in which one sample interval is used and that is used for many samples (e.g., hours, days, weeks) and a curve fit is determined. When different time sample intervals are used, and those are curve fitted compared against other sample intervals earlier, the data converges to a faster resolution.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), property(ies), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skill in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

To aid the Patent Office, and any readers of any patent issued on this application in interpreting the claims appended hereto, applicants wish to note that they do not intend any of the appended claims to invoke paragraph 6 of 35 U.S.C. § 112, U.S.C. § 112 paragraph (f), or equivalent, as it exists on the date of filing hereof unless the words "means for" or "step for" are explicitly used in the particular claim.

For each of the claims, each dependent claim can depend both from the independent claim and from each of the prior dependent claims for each and every claim so long as the prior claim provides a proper antecedent basis for a claim term or element.

What is claimed is:

1. A wearable device comprising:
a computer comprising one or more accelerometers, one or more processors comprising a non-transitory computer-readable medium, wherein the one or more processors are communicably coupled to the one or more accelerometers, an interface, and the wearable device, wherein the one or more accelerometers measure acceleration in a first axis, a second axis, and a third axis, an alarm, and a battery;
wherein the accelerometers monitor in a continuous time basis generate raw data or time-stamped data;
apply a sliding or moving window to the raw data or time-stamped data generated by the accelerometers;
using the raw data or time-stamped data to obtain a daytime energy level and a nighttime energy level;
calculating a difference between the daytime energy level and the nighttime energy level; and
using an XGBoost algorithm modified for categorical analysis by splitting data into trees using a pre-computed number of categories based on the first axis, the second axis, and the third axis measurements, which the trees also include independent dummy variables when no data is available, wherein the modified XGBoost algorithm generates a predicted trajectory of resting and active phase of when there will be little to no day, or night activity levels of the patient; and
when a slope of the predicted trajectory of resting and active phase is negative to trigger the alarm to manage a patient with a pre-determined treatment or intervention selected from waking up the subject, resuscitation, administration of a remedy or medication, administration of a nutritional supplement, administration of a vitamin, exercise, physical therapy, massage, stretching, consumption of food, rest, sleep, and any combination thereof.

2. The device of claim 1, wherein the device is configured to transmit the sliding or moving window applied to the raw data or time-stamped data to a cloud or a Wi-Fi type module, a BLUETOOTH® type module containing storage of the raw data or time-stamped data.

3. The device of claim 1, wherein the device is configured to time-stamp the raw data or time-stamped data in incremental sizes.

4. The device of claim 1, wherein the device is configured to calculate activity levels including a daytime active percentage, a daytime resting percentage, a nighttime active percentage, and a nighttime resting percentage.

5. The device of claim 1, wherein the device is configured to provide a maximum daytime and a minimum nighttime resting energy levels, resting percentage of daytime energy levels, maximum daytime and minimum daytime resting percentage levels minimum nighttime active percentage levels, activity or movement percentage levels, absolute moving percentage levels, R squared and negative slope nighttime energy level increase, daytime activity percentage, nighttime activity percentage, an intersection of any or all of either energy levels or percentage levels, the daytime or nighttime active percentage levels going below the 0% level, the maximum daytime activity percentage levels plus minimum day time resting levels, and/or minimum nighttime active percentage plus a maximum nighttime percentage resting levels.

6. The device of claim 1, wherein the device is configured to measure a particular energy level in a predetermined time period including morning, noon, or night.

7. The device of claim 1, wherein the device is configured to define a day and night active percentage differences as a change in daytime activity level percentage minus the change in nighttime activity percentage.

8. The device of claim 1, wherein the device in configured to define a net daytime active percentage level as a daytime activity percentage minus a daytime resting percentage.

9. The device of claim 1, wherein the device is configured to optimize an adjusted R-squared value and slope using different sampling windows and/or data sampling rates.

10. The device of claim 1, wherein the device uses an exponential regression linear model, linear regression, moving averages and sampling rates to provide additional analyzable results.

11. The device of claim 1, wherein the device uses curve fitting algorithms and/or sampling size for a sampled data set from the accelerometers.

12. The device of claim 1, wherein the device uses the difference in energy levels measured to predict the last living days of a senior.

* * * * *